United States Patent [19]
Yoneda

[11] Patent Number: 6,053,621
[45] Date of Patent: Apr. 25, 2000

[54] LIGHTING UNIT FOR INSPECTING A SURFACE

[75] Inventor: Kenji Yoneda, Kyoto, Japan

[73] Assignee: CCS Co., Ltd., Japan

[21] Appl. No.: 08/997,411

[22] Filed: Dec. 23, 1997

[51] Int. Cl.[7] ..................................... F21V 13/04
[52] U.S. Cl. ............... 362/245; 362/31; 362/311; 362/327; 362/329; 356/237.2
[58] Field of Search ................... 362/26, 27, 31, 362/244, 245, 246, 329, 330, 327, 138, 311; 356/237.2, 237.3, 237.4, 237.5, 394; 359/387, 708, 710, 711

[56] References Cited

U.S. PATENT DOCUMENTS

| | | | |
|---|---|---|---|
| 1,943,510 | 1/1934 | Bauersfeld et al. | 359/387 |
| 3,278,740 | 10/1966 | Madansky | 362/27 |
| 3,409,770 | 11/1968 | Clapham, Jr. | 250/467.1 |
| 3,857,626 | 12/1974 | Rosenberger et al. | 359/387 |
| 4,793,707 | 12/1988 | Hata et al. | 356/375 |
| 4,930,055 | 5/1990 | Swadell | 362/245 |
| 4,991,064 | 2/1991 | Clem | 362/27 |
| 5,136,483 | 8/1992 | Schoniger et al. | 362/31 |
| 5,151,679 | 9/1992 | Dimmick | 362/31 |
| 5,325,231 | 6/1994 | Tamura et al. | 359/387 |
| 5,528,709 | 6/1996 | Koike et al. | 362/31 |
| 5,642,933 | 7/1997 | Hitora | 362/245 |
| 5,690,417 | 11/1997 | Polidor et al. | 359/387 |
| 5,764,391 | 6/1998 | Smith | 362/27 |
| 5,828,449 | 10/1998 | King et al. | 356/237.2 |

*Primary Examiner*—Alan Cariaso
*Attorney, Agent, or Firm*—Banner & Witcoff, Ltd.

[57] ABSTRACT

A lighting unit for examining the quality of a product, wherein the lighting unit can be easily assembled, has a small number of components, and emits light from a surface at a light intensity with little unevenness. An illuminant assembly of the lighting unit comprises a ring-shaped transparent body for light diffusion, and a plurality of illuminants such as light-emitting diodes that are positioned along the periphery of the transparent body and are capable of emitting light toward the center of the transparent body. Light emitted from the illuminants passes through the transparent body while being reflected and scattered, and is emitted uniformly from an underside surface of the transparent body, providing emission of light from a surface at an even light intensity.

8 Claims, 9 Drawing Sheets

LIGHTING UNIT FOR INSPECTING A SURFACE

BACKGROUND OF THE INVENTION

1. Field of the Invention

This invention relates to a lighting unit that is preferably used when a product inspection is conducted by means of reflected light from the lightning unit.

2. Discussion of the Relevant Art

As a method of examining the surface of a product, it has generally been known that a product to be examined is irradiated on its upper side by a lighting unit having an illuminant assembly on its underside, with the reflected light then being visually inspected or photographed in close proximity to the lighting unit. If there is some unevenness in light intensity on the surface to be examined, it may be that a micro flaw or finishing defect on the surface of the product to be examined has failed to be detected. Therefore, in examining a surface of a product it is very common to use a lighting unit having an illuminant assembly of such a construction that the assembly has a plurality of illuminants such as light-emitting diodes positioned all over the underside of the lighting unit, with the entire underside thereof emitting light so as to maintain an even light intensity on the surface to be examined.

However, if a lighting unit has the above construction, a plurality of illuminants must be positioned all over the underside of the lighting unit, greatly increasing the time required to assemble the lighting unit. This not only causes some unevenness in light intensity on the surface to be examined, but also requires precision in assembly of the lighting unit to prevent said unevenness from being caused by unevenness in the assembly orientation of each illuminant. In addition, if the surface to be examined is glossy, the illuminants are reflected, making it impossible to inspect the surface.

It is an object of the present invention to provide a lighting unit characterized by the fact that the lighting unit having a smaller number of illuminants can reduce unevenness in light intensity on a surface of a product to be examined, and by the fact that the illuminants can be set up easily.

SUMMARY OF THE INVENTION

In order to accomplish the above object, the invention has adopted the following lighting unit. The lighting unit in accordance with the present invention comprises a ring-shaped transparent body for light diffusion having a center hole and having a light-emission surface that surrounds the center hole and evenly emits light projected from a plurality of illuminants. The above lighting unit enables both even surface emission of light and reduction of unevenness in light intensity on a surface of a product to be examined.

More specifically, the invention is a lighting unit comprising a ring-shaped transparent body for light diffusion and a plurality of illuminants, with the transparent body having a center hole and having a light-emission surface and a light-introduction surface, both of which surround the center hole, with the plurality of illuminants being located along the light-introduction surface so as to emit light from the light-emission surface of the transparent body.

In particular, in order to reduce unevenness in light intensity near the light-introduction surface to improve light diffusion, and in order to enable illuminants to be mounted, it is preferable to fill the opening between the transparent body and the illuminants with transparent silicone.

In order to efficiently emit light, it is preferable to have a reflective layer on each arbitrary surface other than the light-introduction surface and the light-emission surface so as to reflect and return light into the transparent body.

In order to emit light from a plane, the light-emission surface of the transparent body is preferably a ring-shaped plane.

In order to illuminate a product to be examined from not just one but several directions so as to light all parts of it, the transparent body preferably has a light-emission surface that is a concave face of a hollow truncated cone shape.

In order to illuminate from all directions all parts of a product to be examined, the transparent body preferably has a light-emission surface that is a concave face of a bowl shape.

In the above lighting unit in accordance with the present invention, light emitted by the illuminants is projected into the transparent body, and is reflected and scattered in a complex manner while it is transmitted through the transparent body and uniformly emitted from the light-emission surface of the transparent body at an even intensity. The lighting unit is suitable for examination of a product by means of reflected light. In particular, since the transparent body is in the shape of ring having a center hole, actions such as visual inspection and the taking of photographs can be performed on a product to be examined through the center hole. Furthermore, the above light-emission surface emits light that is more even in intensity than a light-emission surface having no center hole.

If the lighting unit has an opening between the transparent body and the illuminants that is filled with transparent silicone, immediately after light is emitted from the illuminants, the light is deflected and scattered in a complex manner, thereby reducing the directionality of the light and causing the light-emission surface to emit light more uniformly.

If the lighting unit has a reflective layer on each arbitrary surface other than the light-introduction surface and the light-emission surface so as to reflect and return light into the transparent body, since the majority of light is emitted from the light-emission surface, it is possible to enhance the light intensity using the same quantity of light and to emit the same light intensity using a smaller quantity of light from the illuminants.

If the lighting unit comprises a transparent body that has a ring-shaped light-emission plane, the light-emission plane can unidirectionally emit light onto a product to be examined.

If the lighting unit comprises a light-emission surface of the transparent body that is a concave face of a hollow truncated cone shape or a concave face of a bowl shape, illuminating a product to be examined is possible from not just one but several directions so as to light all parts of it, and illuminating a three-dimensional product to be examined is possible with no unevenness in light intensity on the surface of the product.

In accordance with the present invention, the following effects are achieved.

Since a lighting unit in accordance with the present invention comprises a ring-shape transparent body for light diffusion and a plurality of illuminants wherein the transparent body has a center hole and has a light-emission surface and a light-introduction surface both surrounding the center hole and wherein the illuminants are set up along the light-introduction surface, light emitted by the illuminants is reflected and scattered in a complicated manner while passing through the transparent body and can be uniformly emitted from the light-emission surface of the transparent body in an even intensity without difficulty. Therefore, light intensity on a surface of a product to be examined becomes constant and even, the illuminants are not reflected on the surface of the product, and there arises a reduction in failing to detect a micro flaw or a finishing defect on the surface of the product. Owing to reflection and scattering of light through the transparent body, slight deviation in direction of each of the mounted illuminants from an exact alignment may not have significant influence on evenness of light intensity of the transparent body. Therefore, allowance in precision of assembling the illuminants becomes large, resulting in easier assembling work. Since the illuminants are set up along the light-introduction surface only, the number of parts to be used is smaller than that for a lighting unit having illuminants which are set up on a whole underside of a illuminants assembly, resulting in shortened assembling time. Since it is easy to alter angles and shapes of the light-emission surface and the light-introduction surface in designing and to alter color of light to be emitted, it is possible to provide a lighting unit which can emit most suitable light from the light-emission surface for a surface of a product to be examined.

If the above-mentioned lighting unit has an opening between the transparent body and the illuminants which is filled with transparent silicone, immediately after light is emitted from illuminants, the light is complicatedly deflected and scattered, thereby reducing in directionality of light and causing the light-emission surface to emit light more uniformly and in more suitable light intensity on the surface of the product.

If the lighting unit has a reflective layer on each of arbitrary surfaces other than the light-emission surface so as to reflect and return light into the transparent body, since more light is emitted from the light-emission surface only, it is possible to enhance the light intensity by using the same quantity of light and to emit the same light intensity by using a smaller quantity of light from illuminants.

If the light-emission surface of the transparent body is a ring-shape plane, the light-emission surface becomes a plane light source to unidirectionally emit light toward a product to be examined and is preferable in case that a surface to be examined of the product is a plane.

If the lighting unit comprises a light-emission surface which is a concave face of a hollow truncated cone shape or which is a concave face of a bowl shape, lighting up a product to be examined is possible from not only one direction but also several directions as if to cover the product and lighting up a three-dimensional product to be examined is also possible without unevenness in light intensity on the surface of the product.

BRIEF DESCRIPTION OF THE DRAWINGS

The objects and features of the invention may be understood with reference to the following detailed descriptions of illustrative embodiments of the invention, taken together with the accompanying drawings, in which.

DETAILED DESCRIPTION OF THE PREFERRED EMBODIMENTS

A first embodiment of the invention is described below with reference to the accompanying drawings.

Figure 1:
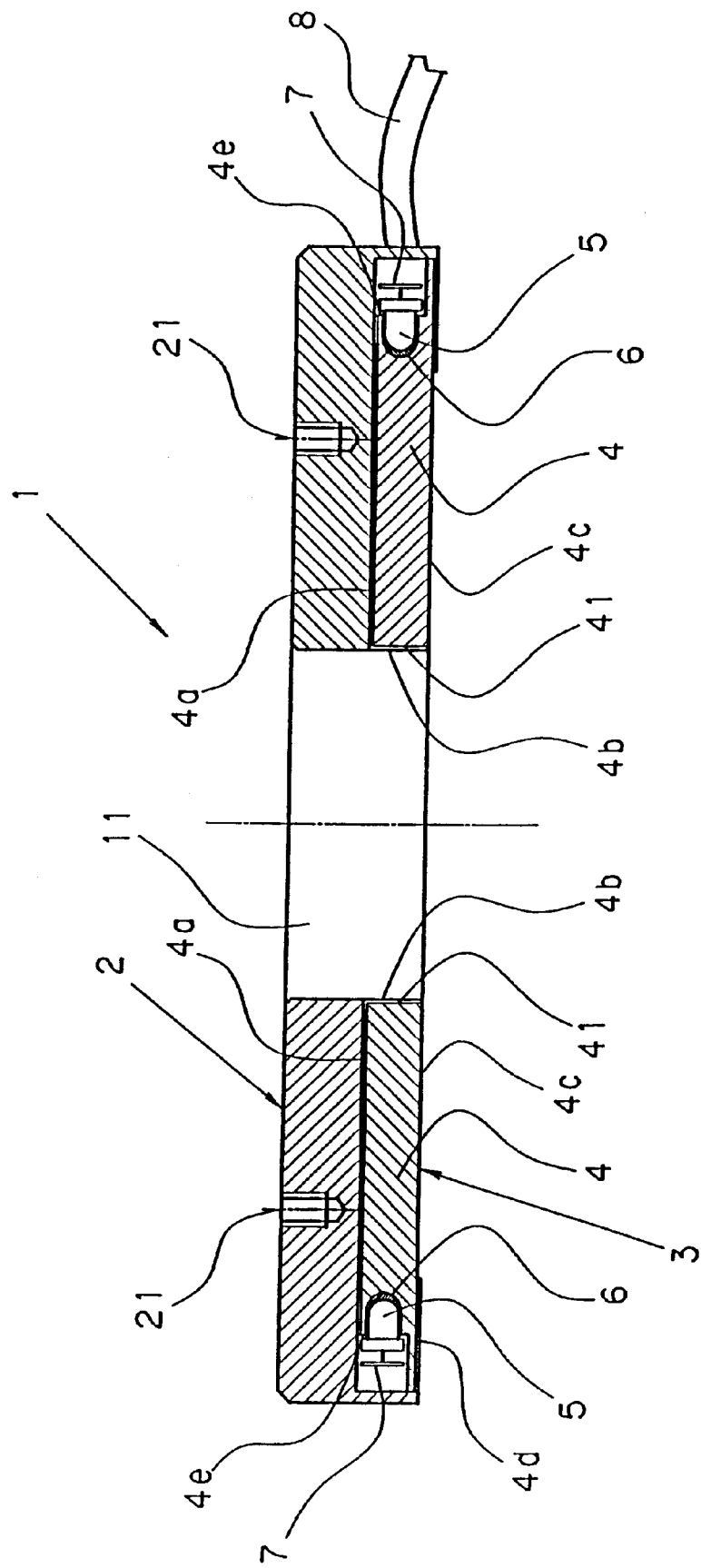
FIG. 1 is a cross-sectional view of a lighting unit showing a first embodiment of this invention.
Figure 2:
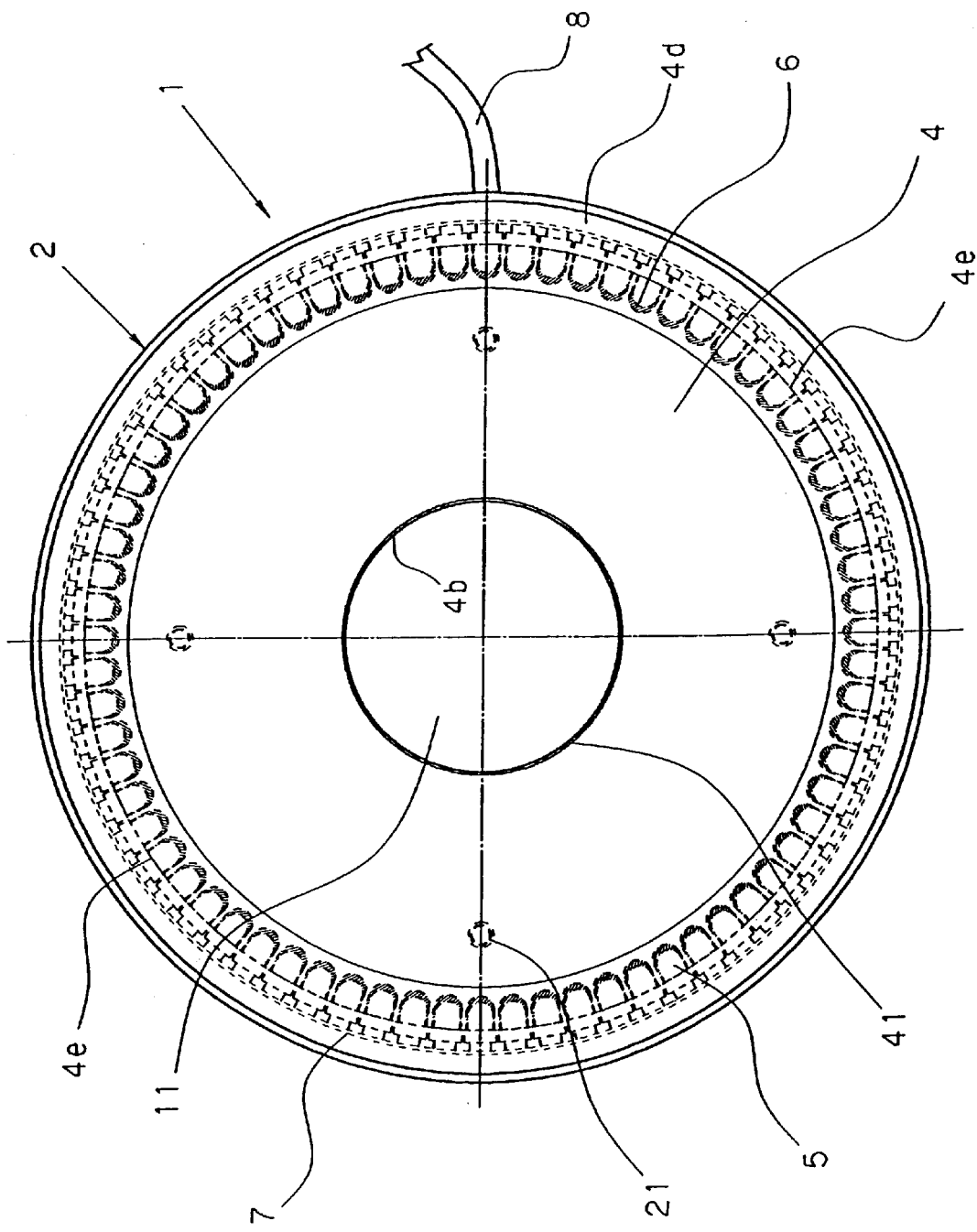
FIG. 2 is a bottom view of a lighting unit showing the first embodiment of this invention.

As shown in FIGS. 1 and 2, a lighting unit 1 comprises a ring-shaped illuminant-assembly holder 2 and an illuminant assembly 3, with the illuminant assembly 3 being held in close contact with the bottom side of the illuminant-assembly holder 2. The illuminant assembly 3 comprises a ring-shaped transparent body 4 and a plurality of illuminants 5 such as light-emitting diodes. The transparent body 4 has a center hole 11 of the same diameter as the illuminant-assembly holder 2. The illuminants 5 are arranged in a row along a light-introduction peripheral surface 4e. Light emitted by the illuminants 5 is projected at a right angle to the axis of the center hole 11. The transparent body 4 has a light-emission plane 4c on the side opposite the side facing the illuminant-assembly holder 2. The lighting unit 1, which is ring-shaped and has a center hole 11, is for actions such as visual inspection and the taking of photographs of a product to be examined, which is located at the underside of the lighting unit 1, from the upper side of the lighting unit 1 through the center hole 11.

In the first embodiment, the illuminants 5 are mounted on a flexible illuminant-mounting substrate 7 and arranged along the light-introduction surface 4e, with the opening between the transparent body 4 and the illuminants 5 being filled with transparent silicone 6. Each of the illuminants 5 is supplied with power from a power cable 8 inserted through the flexible substrate 7. Surfaces other than the light-introduction surface 4 and the light-emission surface 4c, that is, a surface 4a on the side facing the holder 2, an inner surface 4b, and a side edge 4d of the light-emission surface 4c, are coated with a white reflection layer 41. The light-emission surface 4c of the transparent body 4 has fine irregularities like ground glass. Female screw holes 21 on the upper side of the holder 2 are for mounting the lighting unit 1.

Figure 4:
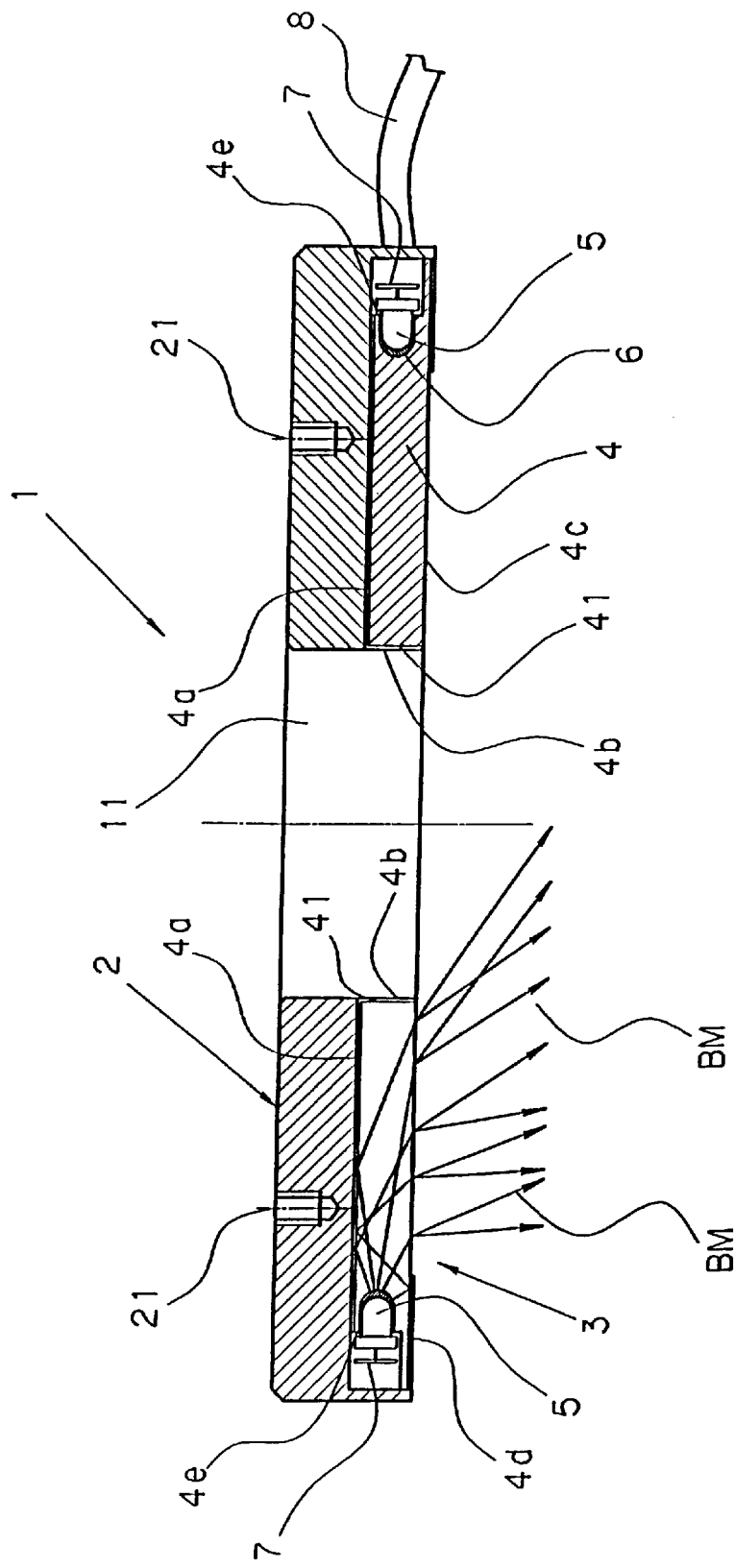
FIG. 4 is a schematic view of light path in a lighting unit of the first embodiment of this invention when the first embodiment is turned on, FIG. 5 is an elevational view of an illuminant-mounting substrate of the first embodiment of this invention on which illuminants are mounted before the first embodiment is assembled.

With the above construction, the lighting unit 1 in accordance with this invention performs as described with the aid of FIG. 4, when the lighting unit 1 is turned on. Light emitted from each of the illuminants 5 is enhanced in terms of its degree of scattering by the transparent silicone 6, and is introduced into the transparent body 4 by the light-introduction surface 4e, and is scattered in vertical and longitudinal directions therein. As shown by a beam BM in FIG. 4, the light is reflected and scattered by the reflection layer 41 applied to the transparent body 4 and partially by the light-emission surface 4c of the transparent body 4, finally being uniformly emitted therefrom. Since the light-emission surface 4c is like ground glass, the light is further scattered thereby and emitted at an even intensity from the entire light-emission surface 4c. With this construction, the total number of illuminants 5 can be made smaller than that in the case of illuminants mounted on the entire illuminant assembly, as specified in the prior art. In addition, even if each of the illuminants 5 deviates slightly in direction from the exact alignment, reflection and scattering of the light tend to eliminate unevenness in the intensity of light emitted from the light-emission surface 4c. Since the thickness of the illuminant assembly 3 can be made close to the external diameter of each of the illuminants 5, the lighting unit 1 can be made small in height.

Figure 5:
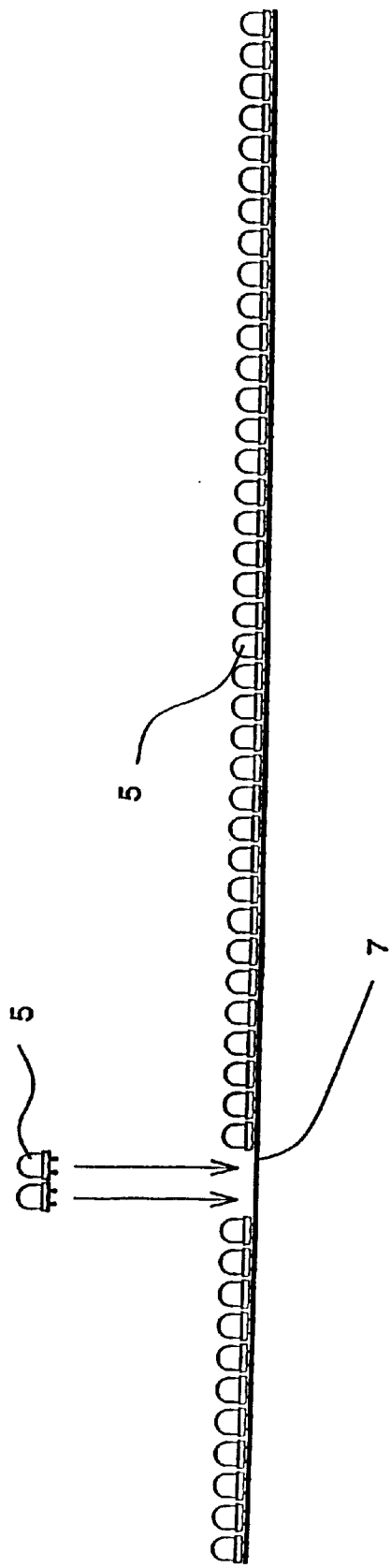
Figure 6:
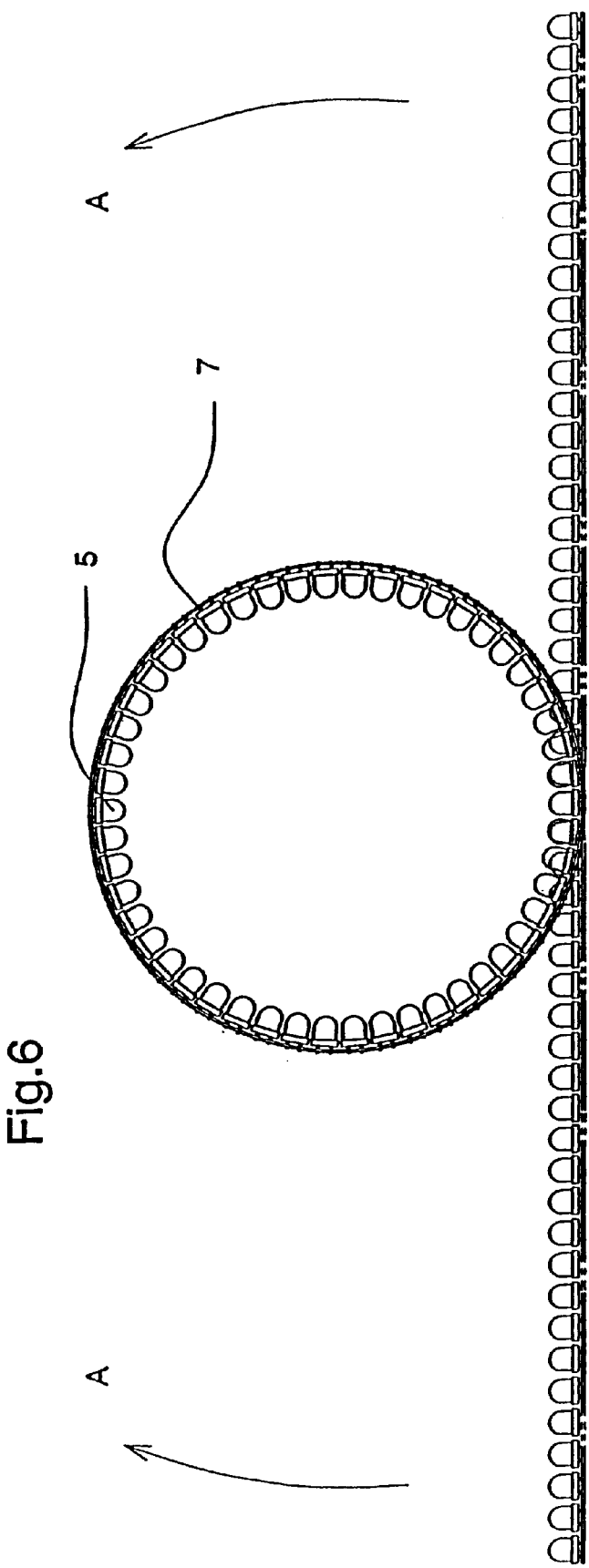
FIG. 6 is an elevational view of an illuminant-mounting substrate of the first embodiment of this invention that is bent in to a circular shape before the substrate is mounted on a periphery of a transparent body.

A method for assembling a lighting unit 1 of the first embodiment, particularly for mounting illuminants 5, is described below with the aid of FIGS. 5 and 6. As shown in FIG. 5, the illuminants 5 are first mounted in a row on a linear flexible illuminant-mounting substrate 7. The substrate 7 that the illuminant 5 is mounted on is then bent and attached to the outer periphery of a transparent body 4 with the light-emission surface facing inside (direction A in FIG. 6). Assembly of the illuminant assembly 3 is completed by filling the opening between the illuminants 5 and the transparent body 4 with transparent silicone 6. A reflection layer 41 may be applied to the transparent body 4 before or after assembly of the illuminants 5 to the transparent body 4. A power cable 8 is attached to the substrate 7 at the same time that the illuminants 5 are mounted as shown in FIG. 5. The illuminant assembly 3 is thus assembled and then mounted on an illuminant-assembly holder 2, and a lighting unit 1 in accordance with this invention is completed. Therefore, mounting of the illuminants 5 on the substrate 7 can be performed by the conventional method for mounting electronic parts on a normal substrate. Furthermore, as described earlier, the total number of the illuminants 5 can be reduced, and slight deviations in the direction of each of the mounted illuminants 5 from the exact alignment may not have a significant influence on the performance of the lighting unit 1 in accordance with this invention. Therefore, there is a reduction in the limitations of assembly, resulting in decreased assembly time and easier assembly work.

A second embodiment of the invention will now be described below with reference to FIG. 3.

Figure 3:
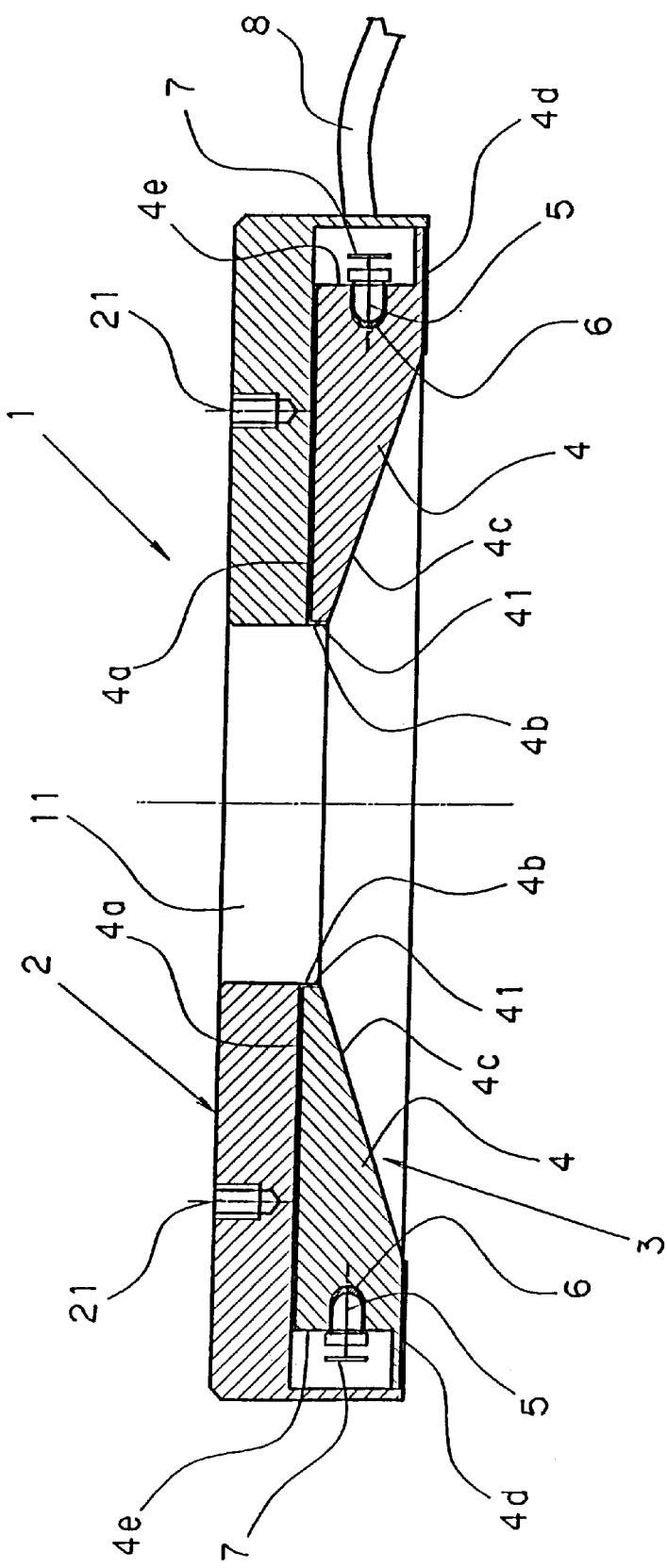
FIG. 3 is a cross-sectional view of a lighting unit showing a second embodiment of this invention.

FIG. 3 shows a lighting unit of the same construction as the first embodiment, except that the light-emission surface 4c of the second embodiment is a concave face of a hollow truncated cone shape. With this construction, since a product to be examined can be illuminated from not just one but several directions so as to light all parts of it, illuminating a three-dimensional product to be examined is possible with no unevenness in light intensity on the surface of the product 9c that the product doesn't cost a shadow.

A third embodiment of the invention is described below with reference to FIG. 7.

Figure 7:
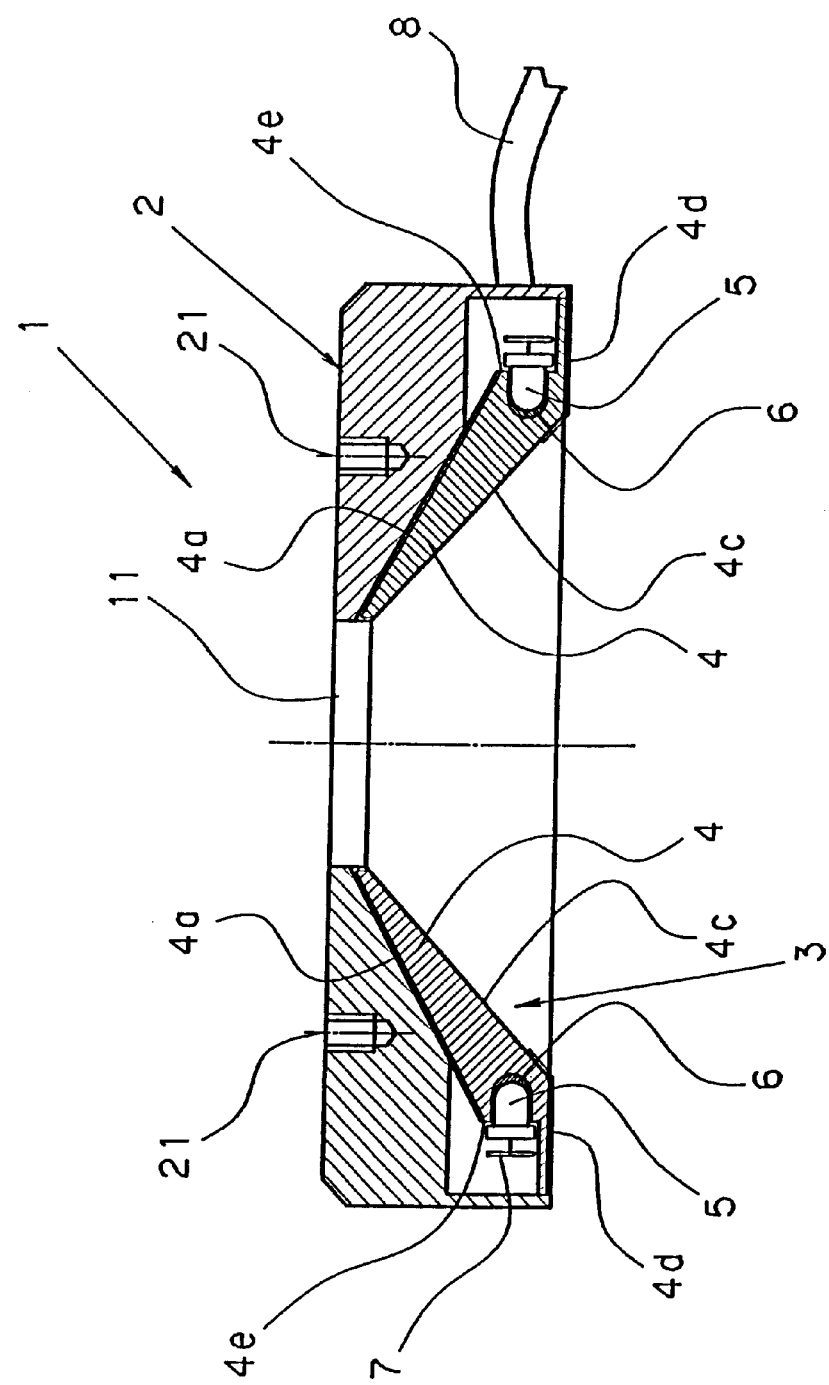
FIG. 7 is a cross-sectional view of a lighting unit showing a third embodiment of this invention.

FIG. 7 shows a lighting unit having a construction that is similar to that of the second embodiment but different in that a transparent body 4 has a surface 4a that is facing a holder 2 and is of a hollow truncated cone shape. This construction is for enhancing light from peripheral directions.

A fourth embodiment of the invention is described below with reference to FIG. 8.

Figure 8:
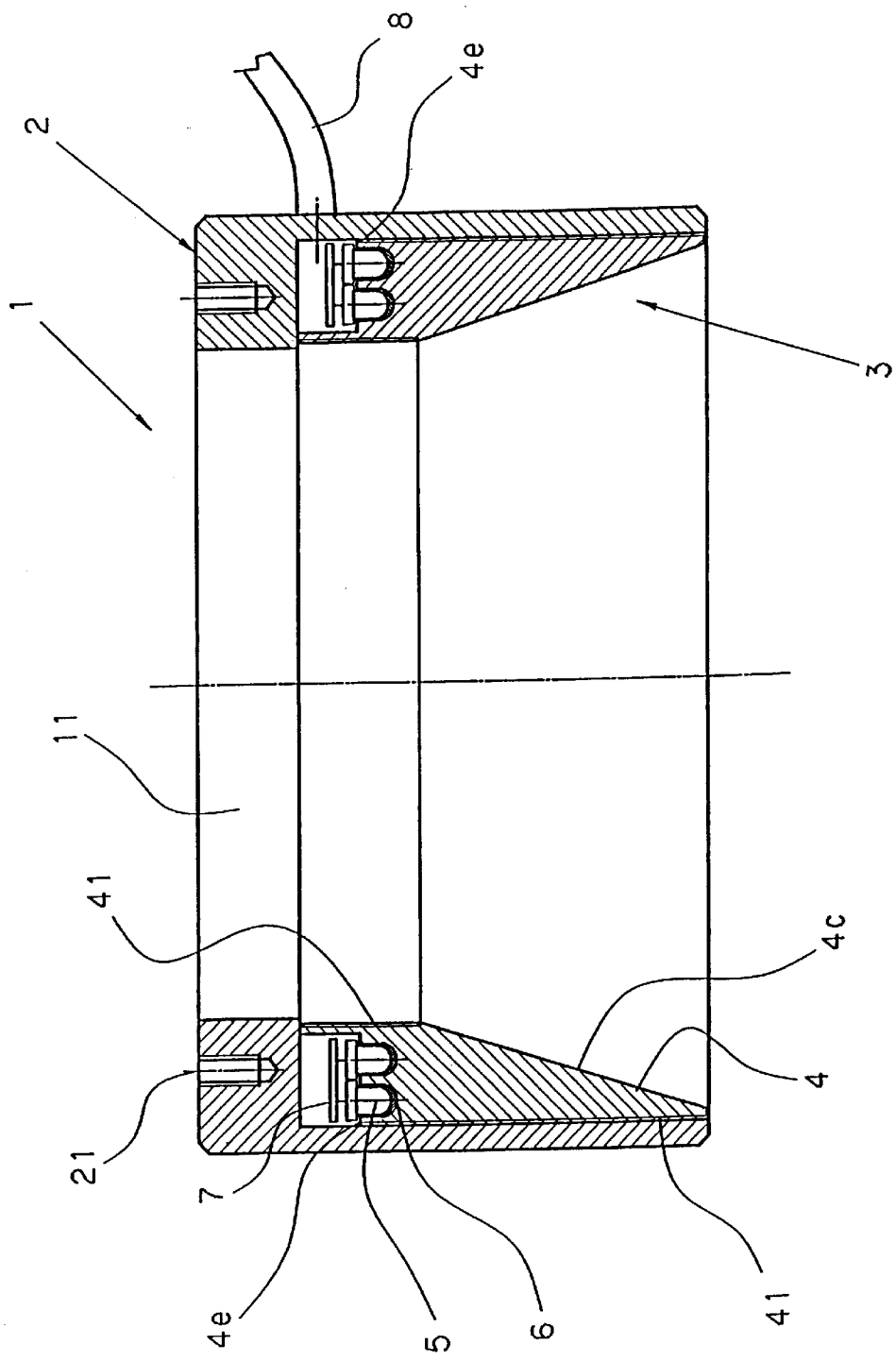
FIG. 8 is a cross-sectional view of a lighting unit showing a fourth embodiment of this invention.

FIG. 8 shows a lighting unit having a construction this similar to the second embodiment but different in that an end face of a transparent body 4 that is facing a holder 2 and is orthogonal to the axis of a center hole 11 is used as a light-introduction surface 4e, and in that light is introduced into the transparent body 4 in a direction that is approximately parallel to the axis of a center hole 11. In the fourth embodiment, as with the second embodiment, it is possible to illuminate a product to be examined from not just one but several directions so as to light all parts of it.

Furthermore, since the mounting substrate 7 is a ring-shaped plane, it is not necessary to use a flexible substrate but is possible to use a normal substrate as a circuit board, making it easier to mount illuminants.

A fifth and final embodiment of the invention is described below with reference to FIG. 9.

Figure 9:
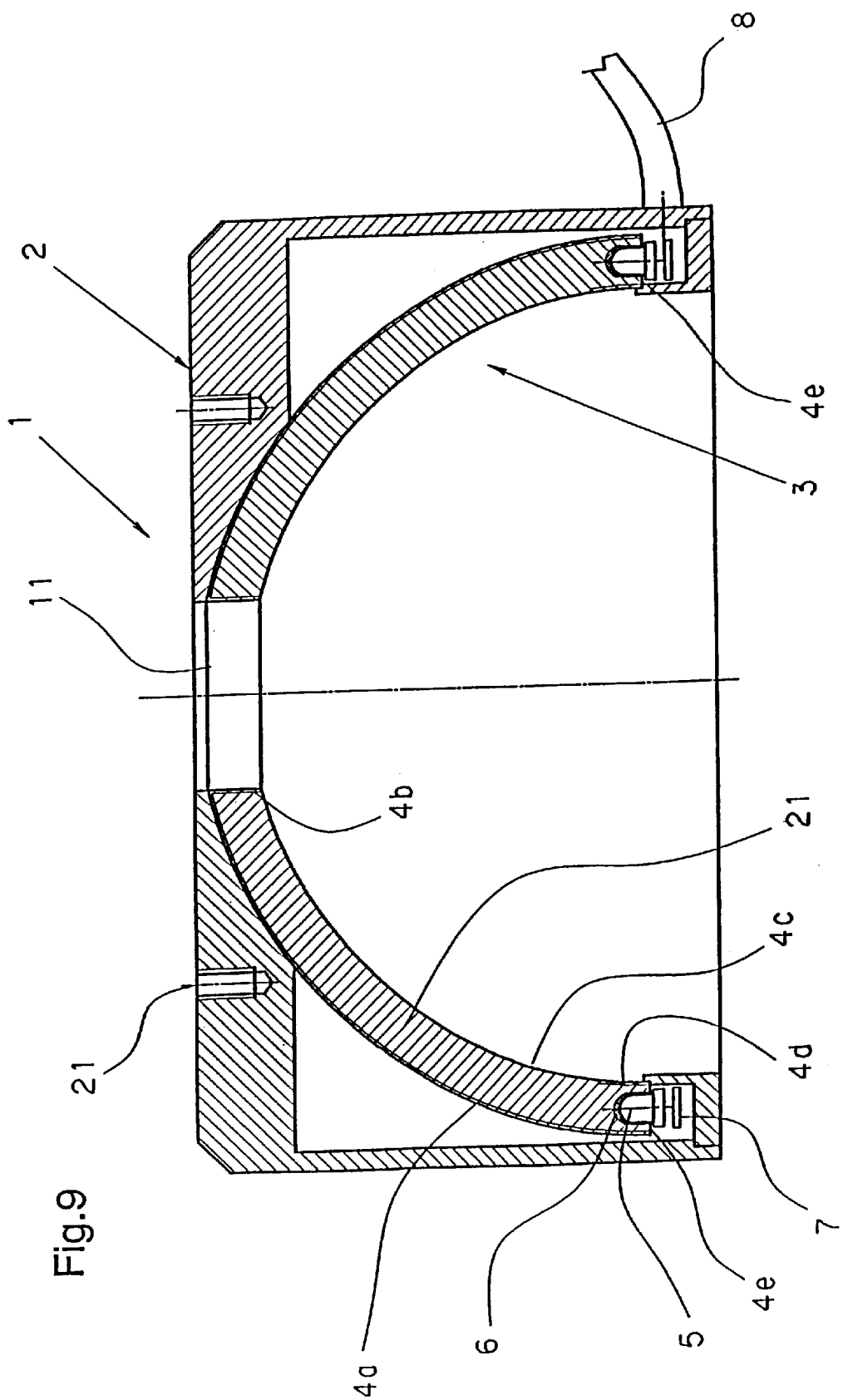
FIG. 9 is a cross-sectional view of a lighting unit showing a fifth embodiment of this invention.

FIG. 9 shows a lighting unit 1 comprising a transparent body 4 of a bowl shape that has an open-ended face approximately orthogonal to the axis of a center hole 11, with the open-ended face serving as a light-introduction surface 4e. In this embodiment, the internal concave surface of the bowl-shaped transparent body is a light-emission surface 4c. Such a construction has an effect similar to that of the fourth embodiment and is preferable particularly when a product to be examined has a spherical surface.

This invention is not limited to the embodiments described in detail hereinabove. For example, a transparent body 4 may be a ring-shaped, while a light-emission surface 4c may only be a concave surface of a bowl shape. Other combinations of the shapes described for the above embodiments may be possible. In order to more preferably illuminate a product to be examined at different positions, a lighting unit may have a transparent body 4 and a light-emission surface 4c of totally different shapes. It is also possible to color a lighting unit. It is further possible to have two or more rows of illuminants 5 in cases in which enhancement of the light intensity is necessary, such as when the illuminants 5 need to be lit in a stroboscopic manner. It is also possible to use a mixture of colors such as red, blue, and green in order to emit colored light from a light-emission surface 4c by changing the mixing ratio. Neither is a light-introduction surface 4e limited to the positions or shapes described in detail hereinabove. A reflective layer 41 is not limited to the color white. Furthermore, transparent silicone 6 may be replaced by a filler of any other material, provided that the filler fulfills the purpose described in detail hereinabove. Without a filler, it may be possible to sufficiently light some products to be examined, although there is some unevenness in light intensity in the proximity of the light-introduction surface 4e of the transparent body 4.

Moreover, none of the constructions is limited to that illustrated in the figures, and various modifications may be made without departing from the spirit and scope thereof.

What is claimed is:

1. A lighting unit comprising a ring-shaped transparent body for light diffusion and a plurality of illuminants, said transparent body having a light-emission surface and a light-introduction surface, said plurality of illuminants extending within said transparent body along said light-introduction surface for emitting light from said light-emission surface and for illuminating a surface of a product to be examined when the product is located at an under side of the lighting unit, said transparent body also including a center hole having a first end and a second end, said center hole being open between said first and second ends for performing visual inspection or taking of photographs of the surface of the product to be examined from an upper side of the lighting unit through the center hole, and a plurality of transparent body surfaces each having a reflective layer so as to reflect and return light into the transparent body.

2. The lighting unit as defined in claim 1, wherein a space between said illuminants and said transparent body is filled with transparent silicone.

3. The lighting unit as defined in claim 1, wherein the light-emission surface of said transparent body is a ring-shaped plane.

4. The lighting unit as defined in claim 1, wherein the light-emission surface of said transparent body is a concave face of a hollow truncated cone shape.

5. The lighting unit as defined in claim 1, wherein the light-emission surface of said transparent body is a concave face of a bowl shape.

6. The lighting unit as defined in claim 2, wherein the light-emission surface of said transparent body is a ring-shaped plane.

7. The lighting unit as defined in claim 2, wherein the light-emission surface of said transparent body is a concave face of a hollow truncated cone shape.

8. The lighting unit as defined in claim 2, wherein the light-emission surface of said transparent body is concave face of a bowl shape.

* * * * *